United States Patent [19]

Hanselmann

[11] Patent Number: 5,756,826
[45] Date of Patent: May 26, 1998

[54] PROCESS FOR PREPARING ACETOACETATES

[75] Inventor: Paul Hanselmann, Visp, Switzerland

[73] Assignee: Lonza, Ltd., Gampel/Valais, Switzerland

[21] Appl. No.: 758,950

[22] Filed: Dec. 3, 1996

[30] Foreign Application Priority Data

Dec. 13, 1995 [CH] Switzerland .............. 3516/95

[51] Int. Cl.$^6$ .................................................. C07C 69/72
[52] U.S. Cl. ........................................ 560/178; 568/307
[58] Field of Search .......................... 560/178; 568/307

[56] References Cited

U.S. PATENT DOCUMENTS 3,554,987  1/1971  Smith .................................... 526/240

FOREIGN PATENT DOCUMENTS 0 013 147   7/1980   European Pat. Off. .
B 0013147   7/1980   European Pat. Off. .

OTHER PUBLICATIONS

El-Abadelah, "6-Fluoro-7 . . .Derivatives", Heterocycles, vol. 41, No. 10, pp. 2203-2219 Oct. 1995.
Sabri et al., "Chiroptical . . .-amines", J. Chem. Soc. Perkin Transaction, vol. 11, pp. 1356-1359 Jul. 1977.

*Primary Examiner*—Gary Geist
*Assistant Examiner*—Rosalynd Keys
*Attorney, Agent, or Firm*—Fisher,Christen & Sabol

[57] ABSTRACT

A process for preparing acetoacetates of the general formula:

$$CH_2=C(R)-C(O)-O-R^1-X-C(O)-CH_2-C(O)-CH_3 \qquad I$$

They are prepared by the addition of diketene onto an alcohol of the general formula:

$$HO-R^1-Y \qquad II$$

and further reaction of the adduct with a compound of the general formula:

$$CH_2=C(R)-C(O)-Z \qquad IV$$

9 Claims, No Drawings

PROCESS FOR PREPARING ACETOACETATES

BACKGROUND OF THE INVENTION

1. Field of the Invention

The invention involves a new process for preparing acetoacetates of the general formula:

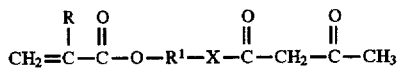

wherein R is hydrogen or methyl, $R^1$ is straight-chain or branched alkylene having from 1 to 12 carbon atoms and X is —O— or —$NR^2$, wherein $R^2$ is hydrogen or alkyl having from 1 to 6 carbon atoms.

2. Background Art

European Published Patent Application No. B 013147 (Example 5) describes the preparation of N-(2-acetoacetamidoethyl) methacrylate by reaction of 2-aminoethyl-methacrylate with diketene. The synthetic principle is based on the addition reaction of an acrylate or methacrylate component with diketene. A great disadvantage of this synthetic principle is that the acrylate or methacrylate component, for example, 2-aminoethyl-methacrylate, is not commercially available and is difficult to obtain. This additional complication considerably reduces the economics of this process of the prior art.

BROAD DESCRIPTION OF THE INVENTION

An object of the invention is to develop an industrially practicable process which starts out from simple building blocks available in industrial amounts. Other objects and advantages of the invention are set out herein or are obvious herefrom to one skilled in the art.

The objects and advantages of the invention are achieved by the process and compounds of the invention.

According to the invention, an alcohol of the general formula:

wherein $R^1$ is as defined above and Y is —OH or —$NHR^2$, wherein $R^2$ is as defined above, is converted by means of diketene into an adduct of the general formula:

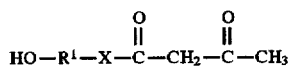

wherein $R^1$ and X are as defined above, and this adduct is finally converted by means of a compound of the general formula:

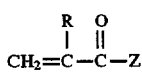

wherein R is as defined above and z is

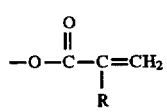

or

wherein R is as defined above, into the end product.

The radicals denoted by $R^1$ and $R^2$ have the following meanings:

The straight-chain or branched alkylene group $R^1$ having from 1 to 12 carbon atoms is advantageously methanediyl or straight-chain or branched ethanediyl, propanediyl, butanediyl, pentanediyl, hexanediyl, heptanediyl, octanediyl, nonanediyl, decanediyl, undecanediyl or dodecanediyl. $R^1$ is preferably a straight-chain or branched alkylene group having from 1 to 6 carbon atoms, in particular, 1,1-ethanediyl, 1,2-ethanediyl, 1,1-propanediyl, 1,2-propanediyl, 1,3-propanediyl, 2-methyl-1,2-propanediyl, 2,2-dimethyl-1,3-propanediyl, 1,4-butanediyl, 1,5-pentanediyl or 1,6-hexanediyl. $R^1$ is particularly preferably 1,1-ethanediyl or 2-methyl-1,2-propanediyl.

The alkyl group $R^2$ having from 1 to 6 carbon atoms is advantageously methyl, ethyl, n-propyl, i-propyl, n-butyl, i-butyl, t-butyl, pentyl or hexyl or an isomer thereof. $R^2$ is preferably hydrogen or methyl.

The addition of diketene onto the alcohol of the general formula II is advantageously carried out at a temperature between 0° C. and 100° C., generally without addition of a solvent. However, it is readily possible, for example, when the alcohol of the general formula II is present as a solid, to use an inert solvent such as an aliphatic alcohol or water.

Particularly suitable alcohols of the general formula II are ethylene glycol, ethanolamine, 2-amino-2-methyl-1-propanol or 2-methylaminoethanol.

The resulting adduct of the general formula III can be isolated by customary methods of the art, but it is usually directly reacted further, without isolation of the intermediate, to give the end product.

The adduct of the general formula III is not known from the literature and is accordingly likewise the subject matter of the invention. The preferred compounds of the general formula III can be derived from the preferred meanings of $R^1$ and $R^2$.

The adduct of the general formula III is advantageously reacted with a compound of the general formula IV in the presence of a polymerization inhibitor, such as, phenothiazine or hydroquinone monomethyl ether or 2,6-di-tert-butyl-p-cresol. The reaction is advantageously carried out at a temperature between –10° C. and 50° C., generally without addition of a solvent. However, here too it is readily possible to use an inert solvent, for example, when the physical state of the compound of the general formula IV demands it.

Particularly suitable compounds of the general formula IV are methacrylic anhydride or acrylic anhydride, in particular methacrylic anhydride.

The target product can be obtained after a reaction time of from 5 to 100 hours. The reaction time can be shortened slightly by adding, for example, 4-dimethylaminopyridine or tributylphosphine. In general, the product can be further used directly together with the by-product, viz. methacrylic acid in the case of the reaction with methacrylic anhydride.

The acetoacetates which can be prepared according to the invention are used as unsaturated monomers for preparing crosslinkable polymers (cf. European Published Patent Application No. B 013147).

EXAMPLE 1

Preparation of (2-acetoacetamido-2-methylpropyl) methacrylate 2-amino-2-methyl-1-propanol (367.59 g, 4.0 mol) was heated to 35° C. and diketene (332.92 g, 3.92 mol) was then added. The addition rate was selected such that the temperature could be held at 35° to 40° C. After 2.5 hours, all of the diketene had been added. The mixture was subsequently cooled to 30° C. The initial melt changed with time into a slightly yellowish, viscose liquid. Thiodiphenylamine (0.69 g, 3.4 mmol) was then added and the dropwise addition of methacrylic anhydride (642.92 g, 3.92 mol) over a period of 5 minutes was commenced as quickly as possible. The reaction was slightly exothermic (up to 34° C.). The mixture was then stirred for 71 hours at 31.5° C. After this time, the conversion of the methacrylic anhydride starting material was 91 percent according to GC. Further thiodiphenylamine (0.69 g, 3.4 mmol) was then added to the orange-brown solution. The solution was then placed in a sample bottle. After further reaction for a total of 163 hours (3 days stirring, 4 days in the sample bottle), the starting material conversion was 96.0 percent.

EXAMPLES 2 TO 8

The reaction was carried out by a method similar to Example 1, but using different alcohols of the general formula II.

| Example | Alcohol (II) R$^1$ | Y | Conversion |
|---|---|---|---|
| 2 | —(CH$_2$)$_2$— | —NH$_2$ | 96 |
| 3 | —(CH$_2$)$_3$— | —NH$_2$ | 95 |
| 4 | —(CH$_2$)$_4$— | —NH$_2$ | 95 |
| 5 | —(CH$_2$)$_5$— | —NH$_2$ | 93 |
| 6 | —(CH$_2$)$_6$— | —NH$_2$ | 92 |
| 7 | —(CH$_2$)$_2$— | —OH | 94 |
| 8 | —(CH$_2$)$_2$— | —NHCH$_3$ | 94 |

What is claimed is:

1. A process for preparing an acetoacetate of the formula:

$$\underset{CH_2=C-C-O-R^1-X-C-CH_2-C-CH_3}{\overset{R\quad O\qquad\quad O\quad\;\; O}{|\;\;\;\;\|\qquad\quad\|\quad\;\;\|}} \quad I$$

wherein R is hydrogen or methyl, R$^1$ is straight-chain or branched alkylene having from 1 to 12 carbon atoms and X is —O— or —NR$^2$, wherein R$^2$ is hydrogen or alkyl having from 1 to 6 carbon atoms, comprising converting an alcohol of the formula:

$$HO-R^1-Y \quad II$$

wherein R$^1$ is as defined above and Y is —OH or —NHR$^2$, wherein R$^2$ is as defined above, by means of diketene into an adduct of the formula:

$$\underset{HO-R^1-X-C-CH_2-C-CH_3}{\overset{O\quad\;\; O}{\|\quad\;\;\|}} \quad III$$

wherein R$^1$ and X are as defined above, and finally converting said adduct by means of a compound of the formula:

$$\underset{CH_2=C-C-Z}{\overset{R\quad O}{|\;\;\;\;\|}} \quad IV$$

wherein R is as defined above and Z is $$-O-\underset{R}{\overset{O}{\underset{|}{\overset{\|}{C}}}}-C=CH_2$$

or $$-\underset{R}{\overset{}{\underset{|}{C}}}=CH_2$$

, wherein R is as defined above, into the end product.

2. The process according to claim 1, wherein the reaction with diketene is carried out at a temperature between 0° C. and 100° C.

3. The process according to claim 2, wherein the reaction with the compound of the formula IV is carried out at a temperature between −10° C. and 50° C.

4. The process according to claim 3, wherein the reaction with the compound of the formula IV is carried out in the presence of a polymerization inhibitor.

5. The process according to claim 4, wherein the compound of the formula IV which is used is methacrylic anhydride.

6. The process according to claim 1, wherein the reaction with the compound of the formula IV is carried out at a temperature between −10° C. and 50° C.

7. The process according to claim 1, wherein the reaction with the compound of the formula IV is carried-out in the presence of a polymerization inhibitor.

8. The process according to claim 1, wherein the compound of the formula IV which is used is methacrylic anhydride.

9. A compound of the formula:

$$\underset{HO-R^1-X-C-CH_2-C-CH_3}{\overset{O\quad\;\; O}{\|\quad\;\;\|}} \quad III$$

wherein R$^1$ is a straight-chain or branched alkylene having 1 to 12 carbon atoms and X is —O—.

* * * * *